US005753262A

United States Patent [19]
Wyse et al.

[11] Patent Number: 5,753,262
[45] Date of Patent: May 19, 1998

[54] CATIONIC LIPID ACID SALT OF 3BETA[N-(N', N'-DIMETHYLAMINOETHANE)-CARBAMOYL]CHOLESTROL AND HALOGENATED SOLVENT-FREE PRELIPOSOMAL LYOPHILATE THEREOF

[75] Inventors: Joseph W. Wyse; Charles D. Warner, both of The Woodlands, Tex.

[73] Assignee: Aronex Pharmaceuticals, Inc., The Woodlands, Tex.

[21] Appl. No.: 485,866

[22] Filed: Jun. 7, 1995

[51] Int. Cl.[6] .......................... A61K 9/133; C12N 15/64; G01N 33/92; C07J 9/00
[52] U.S. Cl. ...................... 424/450; 435/172.1; 436/71; 552/545
[58] Field of Search .................... 424/450; 436/71; 435/172.1; 935/54; 552/545

[56] References Cited

U.S. PATENT DOCUMENTS

| | | | |
|---|---|---|---|
| 4,340,585 | 7/1982 | Borzatta et al. | 424/78.12 |
| 4,544,545 | 10/1985 | Ryan et al. | 424/1.21 |
| 4,624,950 | 11/1986 | Sasaki et al. | 514/223.8 |
| 4,734,417 | 3/1988 | Cousse et al. | 514/255 |
| 5,043,164 | 8/1991 | Huang et al. | 424/423 |
| 5,112,956 | 5/1992 | Tang et al. | 530/424 |
| 5,147,672 | 9/1992 | McCorran et al. | 426/241 |
| 5,149,834 | 9/1992 | Matumoto et al. | 549/292 |
| 5,152,999 | 10/1992 | Tokunaga et al. | 424/450 |
| 5,166,142 | 11/1992 | Moss et al. | 514/54 |
| 5,171,737 | 12/1992 | Weiner et al. | 514/3 |
| 5,174,930 | 12/1992 | Stainmesse et al. | 264/4.6 |
| 5,175,156 | 12/1992 | Boynton et al. | 514/188 |
| 5,200,424 | 4/1993 | Granzer et al. | 514/450 |
| 5,211,976 | 5/1993 | Cox et al. | 426/248 |
| 5,213,829 | 5/1993 | Cox et al. | 426/104 |
| 5,219,599 | 6/1993 | Cox et al. | 426/104 |
| 5,231,112 | 7/1993 | Janoff et al. | 514/401 |
| 5,266,707 | 11/1993 | Matsumoto et al. | 549/292 |
| 5,283,122 | 2/1994 | Huang et al. | 428/402.2 |
| 5,283,185 | 2/1994 | Epand et al. | 435/172.3 |
| 5,290,563 | 3/1994 | Millet-Genin et al. | 424/450 |
| 5,290,565 | 3/1994 | Zysman et al. | 424/450 |
| 5,302,405 | 4/1994 | Hsieh et al. | 426/271 |
| 5,344,650 | 9/1994 | Otsuka et al. | 424/401 |

FOREIGN PATENT DOCUMENTS

9305162  3/1993  WIPO.

OTHER PUBLICATIONS

Amselem et al. Optimization and upscaling of doxorubicin-containing liposomes for clinical use. J. of Pharmaceutical Sciences vol. 79 1045–1052, 1990.

Ford et al. The effect of carbohydrate additives in the freeze–drying of alkaline phosphatase J. Pharm. Pharmacol. vol. 45 86–93, 1993.

"Characterization and Kinetics of MHC Class I–Restricted Presentation of a Soluable Antigen Delivered by Liposomes", Zhou et al., *Immunobiology* vol. 190, pp. 35–52 (1994).

"Cytoplasmic expression of a reporter gene by co–delivery of T7 RNA polymerase and T7 promoter sequence with cationic liposomes" Gao et al., *Nucleic Acids Research*, 1993, vol. 21, No. 12, 2867–2872.

"DNA transfection mediated by cationic liposomes containing lipopoly–lysine: characterization and mechanism of action", Zhou et al, *Biochimica et Biophysica Acta* 1189 (1994) 195–203.

"Effect of cationic cholesterol derivatives on gene transfer and protein kinase C activity", Farhood et al, *Biochimica et Biophysica Acta*, 1111 (1992) 239–246.

"A Novel Cationic Liposome Reagent for Efficient Transfection of Mammaliam Cells", Gao et al., *Biochemical and Biophysical Research Communications*, vol. 179, No. 1, 1991, pp. 280–285.

"HER–2/new targeting gene therapy", Hung et al., *Elsevier Science B.V.* 1994.

"Direct Gene Transfer with DNA–liposome complexes in melanoma: Expression, biologic activity, and lack of toxicity in humans", Nabel et al., *Proc. Natl. Acad. Sci. USA*, vol. 90, pp. 11307–11311.

"Gene Transfer In Vivo with DNA–Liposome Complexes: Lack of Autoimmunity and Gonadal Localization", Nabel et al. *Human Gene Therapy* 3:649–656 (1992).

"Gene Transfer In Vivo with DNA–Liposome Complexes: Safety and Acute Toxicity in Mice", Stewart et al., *Human Gene Therapy* 3:267–275 (1992).

"Immunotherapy of Malignancy by In Vivo gene transfer into tumors" Plautz et al., *Proc. Natl. Acad. Sci. USA*, vol. 90, 4645–4649, May 1993.

"New structures in complex formation between DNA and cationic liposomes visualized by freeze–fracture electron microscopy" Sternberg et al., *FEBS* Letters 356 (1994) 361–366.

HER–2/neu–Targeting Cancer Therapy via Adenovirus–mediated E1A Delivery in an Animal Model, Zhang et al., *Department of Tumor Biology, The University of Texas M.D. Anderson Cancer Center*.

(List continued on next page.)

*Primary Examiner*—James Ketter
*Assistant Examiner*—John S. Brusca
*Attorney, Agent, or Firm*—Lorusso & Loud

[57] ABSTRACT

This invention discloses a novel cationic lipid acid salt of 3β[N-(N',N'-dimethylaminoethane)-carbamoyl]cholesterol. This invention further discloses a transmembrane compatible body suitable for transfection of animals and animal cells with nucleotides such as DNA, RNA, and synthetic nucleotides. Such transmembrane compatible bodies arise from hydratable non-liposomal halogenated solvent-free lyophilate comprising 3β[N-(N',N'-dimethylaminoethane)-carbamoyl]cholesterol and DOPE. This invention yet further discloses a halogenated solvent-free aqueous solution, suitable for lyophilization into a preliposomal powder, wherein the solution comprises 3β[N-(N',N'-dimethylaminoethane)-carbamoyl]cholesterol wherein substantially all 3β[N-(N', N'-dimethylaminoethane)-carbamoyl]cholesterol is dissolved.

13 Claims, 4 Drawing Sheets

OTHER PUBLICATIONS

Liposome–mediated CFTR gene transfer to the nasal epithelium of patients with cystic fibrosis Caplen et al, *Nature Medicine*, vol. 1, No. 1, Jan. 1995.

"Gene Transfer in Mammalian Cells Using Liposomes as Carriers" Singhal et al., Gene Therapeutics: *Methods and Applications of Direct Gene Transfer*, 1994, pp. 118–142.

"Gene therapy for cystic fibrosis in humans by liposome–mediated DNA transfer: the production of resources and the regulatory process" Caplen et al., *Gene Therapy*(1994, pp. 139–147.

"Interaction of phospholipid vesicles with cultured mammalial cells. I. Characteristics of uptake", L. Huang *J–Cell–Biol*. 1975 Oct.; 67(1): 38–48.

"Interaction of phospholipid vesicles with cultured mammalian cells. ll. Studies of Mechanism" RE Pagano, *J–Cell–Biol*. 1975 Oct; 67(1): 49–60.

"Lipid and temperature dependence of membrane–bound ATPase activit;y of *Acholeplasma laidlawii*", JC Hsung, *Can–J–Biochem*. 1974 Nov.; 52(11): 974–80.

"Control of membrane lipid fluidity in *Acholeplasma laidlawii*" L Huang, *FEBS–Lett*. 1974 Jul. 1; 43(1); 1–5.

"Regulation of membrane lipid fluidity in *Acholeplasma laidlawii*: effect of arotenoid pigment content" L Huang, *Biochim–Biophys–Acta*. 1974 Jun. 29; 352(3): 361–70.

Interaction of phospholipid vesicles with cultured mammalian cells RE Pagano, *Nature* 1974 Nov. 8; 252(5479): 166–7.

"Effect of fatty acyl chain length on some structural and functional parameters of Acholeplasma membrane", L Huang, *Can–J–Biochem*. 1974 Jun.; 52(6): 483–90.

"Entrapment of proteins in phosphatidylcholine vesicles" G Adrian, *Biochemistry*. 1979 Dec. 11; 18(25): 5610–4.

"Synthesis and characterization of a new fluorescent phospholipid"BC Chang, *Biochim–Biophys–Acta*. 1979 Sep. 4; 556(1): 52–60.

"Interactions of phospholipid vesicles with murine lymphocytes. II. correlation between altered surface properties and enhanced proliferative response" K Ozato, *Membr–Biochem*. 1978; 1(1–2) 27–42.

Interactions of phospholipid vesicles with murine lymphocytes. I. Vesicle–cell adsorption and fusion as alternate pathways of uptake L Huang, *Membr–Biochem*. 1978; 1(1–2): 1–25.

"Binding of Immunoglobulin G to phospholipid vesicles by Sonication", L. Huang, *Biochemistry*, 1979, May 1; 18(9): 1702–7.

"pH–Sensitive Immunoliposomes Mediate Target–Cell–Specific delivery and Controlled Expression of a Foreign Gene in Mouse" CY Wang, *Proc–Natl–Acad–Sci–U–S–A*, 1987 Nov.; 84(22): 7851–5.

"Solid Core Liposomes with Encapsulated Colloidal Gold Particles" K–Gao, *Biochim–Biophys–Acta*. 1987 Mar. 12; 897(3): 377–83.

"Highly efficient Immunoliposomes Prepared with a Method which is Compatible with various Lipid Compositions", E Holmberg, *Biochem–Biophys–Res–Commun*. 1989 Dec. 29; 165(3): 1272–8.

"Monoclonal Antibody Targeting of Liposomes to Mouse Lung in Vivo" BJ Hughes, *Cancer–Res*. 1989 Nov. 15; 49 (22): 6214–20.

"Role of cholesterol in the Stability of pH–sensitive, large unilamellar liposomes prepared by the Detergent–Dialysis Method" D Liu, *Biochim–Biophys–Acta*. 1989 Jun. 6; 981(2): 254–60.

"Lipid composition is Important for Highly Efficient Target Binding and Retention of Immunoliposomes", K Maruyama, *Proc–Natl–Acad–Sci–U–S–A*. 1990 Aug.; 87(15): 5744–8.

"Partitioning of Teniposide into Membranes and the Role of Lipid Composition" SE Wright, *Biochim–Biophys–Acta*. 1990 Jan. 29; 1021(2): 105–13.

"Structure and Function Relationship of Phosphatidylglycerol in the Stabilization of the Phosphatidylethanolamine Bilayer" A Tari, *Biochemistry*. 1989 Sep. 19; 28(19): 7708–12.

"Small, but no large, Unilamellar Liposomes Composed of bioleoylphosphatidylethanolamine and Oleic Acid can be Stabilized by Human Plasma" DX Liu, *Biochemistry*. 1989 Sep. 19; 28(19): 7700–7.

"Immunoliposomes with Different Acid Sensitivities as Probes for the Cellular Endocytic Pathway" D Collins, *Biochim–Biophys–Acta*. 1989 Dec. 11; 987(1): 47–55.

"The Role of Protein–linked Oligosaccharide in the bilayer stabilization Activity of Glycophorin A for Dioleoylphosphatidylethanolamine Liposomes", P Pinnaduwage, *Biochim–Biophys–Acta* 1989.

"Use of a quaternary ammonium detergent in liposome mediated DNA transfection of mouse L–cells" P Pinnaduwage, *Biochim–Biophys–Acta*. 1989 Oct. 2; 985(1): 33–7.

"Proton and Divalent Cations Induce Synergistic but Mechanistically different Destabilizations of pH–Sensitive Liposomes Composed of dioleoyl phosphatidylethanolamine and oleic acid" D Collins, *Chem–Phys–Lipids*. 1990 Sep.; 55(3): 339–49.

Interactions of Serum Proteins with small unilamellar Liposomes Composed of dioleoylphosphatidylethanolamine and oleic acid: high–density lipoprotein, apolipoprotein A1, and amphipathic peptides stabilize liposomes, D Liu, *Biochemistry*, 1990 Apr. 17; 29(15):3637.

"Structural and Functional Comparisons of pH–sensitive liposomes Composed of Phosphatidylethanolamine and Three Different Diacyl–succinylglycerols" D Collins, *Biochim–Biophys–Acta*. 1990 Jun. 27; 1025(2): 234–42.

"pH–sensitive, Plasma–Stable Liposomes with Relatively prolonged residence in Circulation" D Liu, *Biochim–Biophys–Acta*, 1990 Mar.; 1022(3): 348–54.

"Hydrolysis of Lipid Monolayers and the Substrate Specificity of hepatic Lipase" HM Laboda, *Biochim–Biophys–Acta*, 1986 Apr. 15; 876 (2): 233–42.

"Ca2+ Induced Phase Separations in Phospholipid Mixtures" W Tamura–Lis, *Chem–Phys–Lipids*. 1986 Jan.; 39(1–2): 119–24.

"Destabilization of Phosphatidylethanolamine–Containing liposomes: Hexagonal phase and Asymmetric Membranes", J Bentz, *Biochemistry*. 1987 Apr. 21; 26(8) 2105–16.

"Influence of the Structure of the Lipid–Water Interface on the Activity of Hepatic Lipase" HM Laboda, *Biochemistry*, 1988 Apr. 5; 27(7): 2313–9.

"Intermediary structures during membrane fusion as Observed by Cryo–Electron Microscopy" PM Frederik, *Biochim–Biophys–Acta*. 1989 Feb. 27; 979(2): 275–8.

"Characteristics of Self–Quenching of the Fluorescence of lipid–conjugated Thodamine in membranes" RI MacDonald, *J–Biol–Chem*. 1990 Aug. 15; 265(23): 13533–9.

"Lateral diffusion study of Excimer–forming lipids in lamellar to inverted hexagonal phase trasition of unsaturated phosphatidylethanolamine", SY Chen, Chem–Phys–Lipids. 1990 Mar.

"Target–Sensitive Immunoliposomes: Preparation and Characterization" RJ Ho, Biochemistry, 1986 Sep. 23; 25 (19): 5500–6.

"Tryspin Induced Destabilization of Liposomes Composed of Dioleoylphosphatidylethanolamine and Glycophorin" LR Hu, Biochem–Biophys–Res–Commun. 1986 Dec. 30; 141(3):973–8.

"Biodistribution of pH–Sensitive Immunoliposomes", J. Connor, Biochim–Biophys–Acta. 1986 Dec. 10; 884(3): 474–81.

"Cytotoxicity of Diphtheria Toxin. A. Fragment to Toxin–Resistant Murine Cells Delivered by pH–Sensitive Immunoliposomes" D Collins, Cancer–Res. 1987 Feb. 1; 47(3): 735–9.

"Kinetic and Ultrastructural Studies of Interactions of Target–Sensitive Immunoliposomes with Herpes Simplex Virus", RJ Ho, Biochemistry, 1988 Jan. 12; 27(1): 500–6.

"Characterization of Plasma–Stabilized Liposomes Composed of Dioleoylphosphatidylethanolamine and Oleic Acid", DX Liu, Biochem–Biophys–Res–Commun. 1989 Jul. 14; 162(1): 326–33.

"Lipid Polymorphism as Observed by Cryo–Electron Microscopy" PM Frederik, Biochim–Biophys–Acta. 1991 Feb. 25; 1062(2): 133–41.

"Cell Membranes and Multilamellar Vesicles: Influence of pH on Solvent Induced Damage", MK Jacobsohn, Lipids. 1992 Sep.; 27(9): 694–700.

Prolonged Circulation Time In Vivo of Large Unilamelar Liposomes Composed of Distearoyl Phosphatidylcholine and Cholestrol Containing Amphiphatic Poly(ethylene glycol) K Maruyama, Biochim–Biophys–Acta. 1992 Sep. 22; 1128(1): 44–9.

"The Influence of Cholesterol 3–Sulphate on Phase Behaviour and Hydrocarbon Order in Model Membrane Systems" N Kitson, Biochim–Biophys–Acta. 1992 Oct. 19; 1111(1): 127–35.

"Chemical Exchange Between Lamellar and Non–Lamellar Lipid Phases. A one–and two–dimensional 31P–NMR Study", DB Fenske Biochim–Biophys–Acta. 1992 Jul. 27; 1108(2): 201–9.

"Processing of Exogenous Liposome–Encapsulated Antigens In Vivo Generates Class I MHC–Resricted T Cell Responses" DS Collins, J–Immunol. 1992 Jun. 1; 148(11): 3336–41.

"Sensitivity of Phospholipase C (Bacillus cereus) Activity to Lipid Packing in sonicated Lipid Mixtures", NM Rao, Biochemistry. 1993 Aug. 24; 32(33): 8547–52.

"Immunoliposome Labeling: A sensitive and Specific Method for Cell Surface Labeling", A Huang, J–Immunol–Methods. 1981; 46(2): 141–51.

"Cell–Mediated Immunity to Herpes Simplex Virus: Induction of Cytotoxic T Lymphocyte Responses by Viral Antigens Incorporated into Liposomes", MJ Lawman, J–Immunol. 1981 Jan.; 126(1): 304–8.

Monoclonal Antibody Covalently Coupled with Fatty Acid, A Reagent for in vitro liposome targeting, A Huang, J–Biol–Chem 1980 Sep. 10; 255(17): 8015–8.

"Transfer of Torpedo Acetylcholine Receptors to Mouse L–Cell Surface Membranes by Liposomes Containing Sendai Virus Envelope Proteins." SC Ho, Eur–J–Cell–Biol. 1982 Jun.; 27(2) 221–9.

"In Vivo Induction of Anti–Herpes Simplex Virus Immune Response by Type 1 Antigens and Lipid A Incorporated into Liposomes", PT Naylor, Infect–Immun. 1982 Jun.; 36(3):1209–16.

"Use of Radiolabeled Hexadecyl Cholesteryl Ether as a Liposome Marker", GL Pool, Lipids. 1982 Jun.; 17(6): 448–52

"An improved method for covalent attachment of antibody to liposomes", DF Shen, Biochim–Biophys–Acta. 1982 Jul. 14; 689(1): 31–7.

"Interactions of Immunoliposomes with Target Cells", A Huang, J–Biol–Chem. 1982 Nov. 25; 258(22): 14034–40.

"Incorporation of Acylated Wheat Germ Agglutinin Into Liposomes", S Carpenter–Green; Anal–Biochem. 1983 Nov.; 135(1): 151–5.

"A Novel Cytochemical Marker for Liposome Decomposition in Lysosomes". SC Ho, J–Histochem–Cytochem. 1983 Mar.; 31(3): 404–10.

"Thermotropic and Dynamic Characterization of Interactions of Acylated Alpha–Bungarotoxin with Phospholipid Bilayer Membranes"., B Babbitt, Biochemistry, 1984 Aug. 14; 23(17): 3920–6.

"pH–Sensitive Liposomes: Acid–induced Liposome Fusion". J Connor, Proc–Natl–Acad–U–S–A. 1984 Mar.; 81(6): 1715–8.

"Polyhistidine Mediates an Acid–Dependent Fusion of Negatively Charged Liposomes" CY Wang, Biochemistry, 1984 Sep. 11; 23(19): 4409–16.

"Sendai Virus Induced Leakage of Liposomes Containing Gangliosides", YS Tsao, Biochemistry. 1985 Feb. 26; 24(5): 1092–8.

"Interactions of Antigen–Sensitized Liposomes with Immobilized Antibody: A Homogeneous Solid–Phase Immunlliposome Assay." RJ Ho, J–Immunol. 1985 Jun.; 134(6): 4035–40.

"Effects of Valency on Thermodynamic Parameters of Specific Membrane Interactions", BP Babbitt, Biochemistry. 1985 Apr. 23; 24(9): 2186–94.

"Incorporation of Acylated Antibody into Planara Lipid Multilayers: Characterization and Cell Binding," L Huang, Biochemistry. 1985 Jan. 1; 24(1): 29–34.

"Alpha–Bungarotoxin Immobilized and Oriented on a Lipid Bilayer Vesicle Surface". B Babbitt, Biochemistry. 1985 Jan. 1; 24(1): 15–21.

"Preparation and Characterization of Heat–Sensitive Immunoliposomes", SM Sullivan, Biochim–Biophys–Acta. 1985 Jan. 10; 812(1): 116–26.

"Kinetic Studies of Sendai Virus–Target Membrane Interactions Independent Analysis of Bindging and Fusion," YS Tsao, Biochemistry. 1986 Jul. 1; 25(13): 3971–6.

"Destablization of Target–Sensitive Immunoliposomes by Antigen binding—a Rapid Assay for Virus", RJ Ho, Biochem–Biophys–Res–Commun. 1986 Jul. 31; 138(2): 931–7.

Stimulation of Superoxide Release in Neutrophils by 1–oleoyl 2–acetylglycerol Incorporated into pH–sensitive Liposomes. BE Tsusaki, Biochem–Biophys–Res–Commun. 1986 Apr. 14; 136(1) 242–6.

Targeting of drug loaded Immunoliposomes to Herpes Simplex Virus Infected Corneal Cells: An Effective means of inhibiting Virus Replication in vitro. SG Norley, J–Immunol 1986 Jan.; 136(2): 681–5.

"Immunoliposomes: Preparation; Properties, and Applications" SM Sullivan; Med Res Rev. 1986 Apr. Jun.; 6(2): 171–95.

"Enhanced Delivery to Target Cells by Heat–Sensitive Immunoliposomes". SM Sullivan, Proc–Natl–Acad–Sci–U–S–A. 1986 Aug.; 83(16): 6117–21.

"pH Sensitive Immunoliposomes as an Efficient and Target–Specific Carrier for Antitumor Drugs." J Connor, Cancer–Res. 1986 Jul.; 46(7): 3431–5.

"Interactions of Target–Sensitive Immunoliposomes with Herpes Simplex Virus. The Foundation of a Sensitive Immunoliposome Assay for the Virus." RJ Ho, J–Biol–Chem. 1987 Oct. 15; 262(29): 13979–84.

"Target–Sensitive Immunoliposomes as an Efficient Drug Carrier for Antiviral Activity" RJ Ho, J–Biol–Chem. 1987 Oct. 15; 262(29): 13973–8.

"Inhibition of Herpes Simplex Virus Replication in the Mouse Cornea by Drug Containing Immunoliposomes" SG Norley, Invest–Ophthalmol–Vis–Sci. 1987 Mar.; 28(3): 591–5.

"Gadolinium–Labeled Liposomes: Targeted MR Contrast Agents for the Liver and Spleen," G Kabalka, Radiology. 1987 Apr.; 163(1): 255–8.

"Plasmid DNA adsorbed to pH–Sensitive Liposomes Efficiently Transforms the Target Cells." CY Wang; Biochem–Biophys–Res–Commun. 1987 Sep. 30; 147(3): 980–5.

"The role of Multivalency in Antibody Mediated Liposome Targeting." KS Houck, Biochem–Biophys–Res–Commun. 1987 Jun 30; 145(3): 1205–10.

"Thermodynamic and Phase Characterization of Phosphatidylethanolamine and ganglioside GD1a mixtures." YS Tsao, Biochim–Biophys–Acta. 1987 Jun. 12; 900(1): 79–87.

"beta–Galactosidase–Induced Destabilization of Liposome Composed of Phosphatidylethanolamine and Ganglioside GM1" P Pinnaduwage Biochim–Biophys–Acta. 1988 Apr. 7; 939(2): 375–82.

"A homogeneous, Liposome–based Signal Amplification for Assays Involving Enzymes." P Pinnaduwage, Clin–Chem. 1988 Feb.; 34(2): 268–72.

"Gadolinium–labeled Liposomes Containing Paramagnetic Amphipathic Agents: Targeted MRI Contrast Agents for the Liver." GW Kabalka, Magn–Reson–Med. 1988 Sep.; 8(1): 89–95.

"Highly efficient DNA Delivery Mediated by pH–Sensitive Immunoliposomes." CY Wang, Biochemistry. 1989 Nov 28; 28(24): 9508–14.

"Influence of peptide acylation, liposome Incorporation, and Synthetic Immunomodulators on the Immunogenicity of a 1–23 peptide of glycoprotein in D of herpes simplex virus. Implications for Subunit Vaccines." K Brynestad, J–Virol. 1990 Feb.; 64(2): 680–5.

"Characterization of in vivo immunoliposome Targeting to Pulmonary endothelium", K Maruyama, J–Pharm–Sci. 1990 Nov.; 79(11): 978–84.

"Gd–Labeled Liposomes Containing amphipathic Agents for Magnetic resonance imaging.", GW Kabalka, Invest–Radiol. 1990 Sep.; 25 Suppl 1: S63–4.

"Amphipathic Polyethyleneglycols Effectively Prolong the Circulation Time of Liposomes." AL Klibanov. FEBS–Lett. 1990 Jul. 30; 268(1): 235–7.

"An Improved Method of Loading pH–Sensitive Liposomes with Soluble Proteins for Class I Restricted antigen Presentation.", F Zhou, J–Immunol–Methods. 1991 Dec. 15; 145(1–2): 143–52.

"Proteins and Peptides Bound to Long–Circulating Liposomes." K Maruyama, Biochim–Biophys–Acta, 1991 Nov. 18: 1070(1): 246–52.

"Targeting of Macromolecular carriers and Liposomes by Antibodies to Myosin Heavy chain." AL Klibanov, AM–J–Physiol. 1991 Oct.; 261 (4 Suppl): 60–5.

"Gadolinium–labeled Liposomes Containing Various Amphiphilic Gd–DTPA Derivatives: Targeted MRI Contrast Enhancement Agents for the Liver" GW Kabalka, Magn–Reson–Med. 1991 Jun.; 19(2): 406–15.

"Gadolinium–Labeled Liposomes Containing Amphiphilic Gd–DTPA Derivatives of Varying Chain Length: Targeted MRI Contrast enhancement Agents for the Liver." GW Kabalka, Magn–Reson–Imaging. 1991; 9(3): 373–7.

"pH Sensitive Liposomes Provide an Efficient Means of Sensitizing Target Cells to Class I Restricted CTL Recognition of a Soluble Protein." R Reddy, J–Immunol–Methods. 1991 Aug. 9; 141(2): 157–63.

"Large Liposomes Containing Ganglioside GM1 Accumulate Effectively in Spleen." D Liu; Biochim–Biophys–Acta. 1991 Jul. 22; 1066(2): 159–65.

"Influence of the Steric Barrier Activity of Amphipathic poly(ethyleneglycol) and Ganglioside GM1 on the Circulation Time of Liposomes and on the Target Binding of Immunoliposomes In Vivo.", A Mori, FEBS–Lett. 1991 Jun. 24; 284(2).

"Activity of Amphiphathic poly(ethylene glycol) 5000 to Prolong the Circulation Time of Liposomes Depends on the Liposome Size and is Unfavorable for Immunoliposome Binding to Target", AL Klibanov, Biochim–Biophys–Acta. 1991 Feb. 25; 1062(2): 142–8.

"Stable Target–Sensitive Immunoliposomes." P Pinnaduwage, Biochemistry 1992 Mar. 24; 31(11): 2850–5.

"Interaction of Synthetic Glycophospholipids with Phospholipid Bilayer membranes." YS Park, Biochim–Biophys–Acta. 1992 Dec. 9; 1112(2): 251–8.

"Prolonged Survival of Thymoma–Bearing Mice After Vaccination with a Soluble Protein Antigen Entrapped in Liposomes: A Model Study." F Zhou; Cancer–Res. 1992 Nov. 15; 52(22): 6287–91.

"Induction of Cytotoxic T Lymphocytes In Vivo with Protein Antigen Entrapped in Membranes Vehicles." F Zhou; J–Immunol. 1992 Sep. 1; 149(5): 1599–604.

"Class I Restricted CTL Recognition of a Soluble Protein Delivered by Liposomes Containing Lipophilic Polylysines." S Nair; J–Immunol–Methods. 1992 Aug. 10; 152(2): 237–43.

"Soluble Proteins delivered to Dendritic cells Via pH–Sensitive Liposomes Induce Primary Cytotoxic T Lymphocyte Responses In Vitro." S Nair, J–ExpMed. 1992 Feb. 1; 175(2): 609–12.

"Amphiphathic Poly(ethylene glycol) 5000 Stabilized Dioleoyl–phosphatidylethanolamine Liposomes Accumulate in Spleen." DC Litzinger Biochim–Biophys–Acta. 1992 Aug. 19; 1127(3): 249–54.

"Phosphatidylethanolamine Liposomes: Drug delivery, Gene Transfer and Immunodiagnostic Applications." DC Litzinger, Biochim–Biophys–Acta. 1992 Aug. 14; 1113(2): 201–27.

"Some Negatively Charged Phospholipid Derivatives Prolong the Liposome Circulation In Vivo." YS Park, Biochim–Biophys–Acta. 1992 Jul. 27; 1108(2): 257–60.

"Cationic Liposomes Enhance Targeted Delivery and Expression of Exogenous DNA Mediated by N–Terminal Modified Poly(L–lysine)–Antibody Conjugate in Mouse Lung Endothelial cells." VS Trubetskoy; Biochim–Biophys–Acta. 1992 Jul. 15; 1131(3): 311–3.

"Trypsin–Induced Lysis of Lipid Vesicles: Effect of Surface Charge and Lipid Composition." D Liu; Anal–Biochem. 1992 Apr.; 202(1): 1–5.

"Targeted Accumulation of Polyethylene Glycol–Coated Immunoliposomes in Infarcted Rabbit Myocardium." VP Torchilin; FASEB–J. 1992 Jun.; 6(9): 2716–9.

"Cryoprotective Activity of Synthetic Glycophospholipids and Their Interactions with Trehalose." YS Park, Biochim–Biophys–Acta. 1992 Mar. 25; 1124(3): 241–8.

"Role of Liposome Size and RES Blockade in Controlling Biodistribution and Tumor Uptake of GM1–Containing Liposomes." D Liu; Biochim–Biophys–Acta. 1992 Feb. 17; 1104(1): 95–101.

"Biodistribution and Immunotargetability of Ganglioside–Stabilized dioleoylphosphatidylethanolamine Liposomes." DC Litzinger, Biochim–Biophys–Acta. 1992 Feb. 17; 1104(1): 179–87.

"In Vivo Cytotoxic T Lymphocyte Induction with Soluble Proteins Administered in Liposomes." R Reddy; J–Immunol. 1992 Mar. 1; 148(5): 1585–9.

"Potentiation of the Humoral Response of Intravenous Antigen by Splenotropic Liposomes." DX Liu; Immunol–Lett. 1992 Feb.; 31(2): 177–81.

"Bilayer Stabilization of Phosphatidylethanolamine by L–biotinyl–phosphatidylethanolamine." SE Wright; Biochim–Biophys–Acta. 1992 Jan. 10; 1103(1): 172–8.

"Contact–dependent, Immunecomplex–Mediated Lysis of Hapten–Sensitized Liposomes." B Babbitt; Biocon-jug–Chem. 1993 May–Jun.; 4(3): 199–205.

"Immunotargeting of Liposomes Containing Lipophilic Antitumor Prodrugs." A Mori; Pharm Res. 1993 Apr.; 10(4): 507–14.

"Effect of chemically Modified GM1 and Neoglycolipid Analogs of GM1 on Liposome Circulation Time: Evidence Supporting the Dysopsonin hypothesis." YS Park; Biochim–Biophys–Acta. 1993 Feb. 10; 1166(1): 105–14.

"Distribution within the Organs of a Reticuloendothelial System of Liposomes Containing Lipid A." YS Park; J–Drug–Target. 1993; 1(4): 325–30.

"Cationic Liposomes for Direct Gene Transfer In Therapy of Cancer and Other Diseases." H Farhood; Ann–N–Y–Acad–Sci. 1994 May 31; 716: 23–34; discussion 34–5.

"Interactions of Liposome Bilayers Composed of 1,2–diacyl–3–succinyl–glycerol within Protons and Divalent cations." AM Tari; Biochim–Biophys–Acta. 1994 Jun 22; 1192(2): 253–62.

"Nasal Application of the cationic Liposome DC–Chol: DOPE does not Alter Ion Transport, Lung Function or Bacterial Growth." PG Middleton Eur–Respir–J. 1994 Mar.; 7(3): 442–5.

"A Sustained, Cytoplasmic Transgene Expression System Delivered by Cationic Liposomes." X Gao; Biochem–Biophys–Res–Commun. 1994 May 16; 200(3): 1201–6.

"Effect of Liposome Size on the Circulation Time and Intraorgan Distribution of Amphipathic Poly(ethylene glycol)–Containing Liposomes." DC Litzinger; Biochim–Biophys–Acta. 1994 Feb. 23; I190(1): 99–107.

"Monophosphoryl Lipid A Enhances Specific CTL Induction by a Soluble Protein Antigen Entrapped in Liposomes." F Zhou; Vaccine. 1993; 11(11): 1139–44.

FIG. I

CATIONIC LIPID ACID SALT OF 3BETA[N-(N', N'-DIMETHYLAMINOETHANE) - CARBAMOYL]CHOLESTROL AND HALOGENATED SOLVENT-FREE PRELIPOSOMAL LYOPHILATE THEREOF

FIELD OF THE INVENTION

This invention discloses a novel cationic lipid acid salt of 3β[N-(N',N'-dimethylaminoethane)-carbamoyl]cholesterol. This invention further discloses a transmembrane compatible body suitable for transfection of animals and animal cells with nucleotides such as DNA, RNA, and synthetic nucleotides. Such transmembrane compatible bodies arise from hydratable non-liposomal, halogenated solvent-free lyophilate comprising 3β[N-(N',N'-dimethylaminoethane)-carbamoyl]cholesterol. This invention yet further discloses a halogenated solvent-free aqueous solution suitable for lyophilization into a preliposomal powder, wherein the prelyophilate solution comprises 3β[N-(N',N'-dimethylaminoethane)-carbamoyl]cholesterol and dioleoyl phosphatidylethanolamine (DOPE) wherein substantially all 3β[N-(N',N'-dimethylaminoethane)-carbamoyl]cholesterol and DOPE are dissolved.

BACKGROUND OF THE INVENTION

Liposomal gene therapy (a concept which includes transfection or gene delivery) is a powerful mechanism for the delivery of DNA and RNA as well as synthetic congeners thereof. In particular instances, the nucleic acid so delivered is bioactive as antisense, missense, nonsense, as protein producers, on and off and rate regulatory switching for protein or peptide production. Such delivery is frequently for therapeutic or diagnostic purposes in or directed to humans and human cells, and more broadly to animals, animal cells, and the disease and/or metabolic states of animals and animal cells. In this context, the term "animals" is expansively understood to included the entire Kingdom Animalia.

The fields of liposome and gene research have dramatically changed since the introduction of cationic liposomes in 1987 (Felgner et al., Proc. Natl. Acad. Sci. U.S.A., 84:7413–7417 (1987)). Liposomal DNA delivery has been noted in Brigham et al. Am. J. Respir. Cell. Mol. Biol., 1:95–100 (1989); Burger et al. Proc. Natl. Acad. Sci. U.S.A., 89:2145–2149 (1992); Felgner and Ringold, Nature, 337:387–388 (1989); and, Muller et al., DNA Cell Biol., 9:221–229 (1990). Malone et al., disclose mRNA delivery Proc. Natl. Acad. Sci. U.S.A., 86:6077–6081 (1989), as does Weiss et al., J. Virol., 63:5310–5318 (1989). Protein delivery is discussed in Debs et al., J. Biol. Chem, 265:10189–10192 (1990); Nair et al., J. Exp. Med. 175:609–612 (1992); and Walker, Proc. Natl. Acad. Sci. U.S.A., 89:7915–7919 (1992). Delivery of antisense oligomers is reported by Bennett et al., Mol. Pharmacol., 41:1023–1033 (1992); and Chiang et al., J. Biol. Chem., 266:18162–18171 (1991). Particular liposomal formulations are cited in Felgner et al., J. Biol. Chem., 269:2550–2561 (1994); Levintis and Silvius, Biochem. Biophys. Acta, 1023:124–132 (1990); and, Ito et al. Biochem. Intl., 22:235–241 (1990).

U.S. Pat. No. 5,283,185 to Epand et al., discloses 3β[N-(N',N'-dimethylaminoethane)-carbamoyl]cholesterol in basic form for use in transfection. Basic 3β[N-(N'N'-dimethylaminoethane)-carbamoyl]cholesterol (DC-chol A) is not soluble in aqueous solutions. Previous reports of DC cholesterol misattribute a positive charge to the nitrogen of the dimethylamine, which is, in fact neutral. (FIG. 1)

Preparing a liposome suspension of 3β[N-(N',N'-dimethylaminoethane)-carbamoyl]cholesterol from all previously available aqueous insoluble forms required preparation from a dried thin film. This process required solubilization of the basic 3β[N-(N',N'-dimethylaminoethane)-carbamoyl]cholesterol in chloroform, a halogenated solvent. For pharmaceutical applications, residues of halogenated solvents cannot be practically removed from a preparation after being introduced. The inability to provide a halogen-free preparation has hampered the development of 3β[N-(N',N'-dimethylaminoethane)-carbamoyl]cholesterol for use in liposome-type transfecting therapy as a transfecting agent.

Sterile preparation of a liposomal suspension, in some instances (such as from a thin film preparation), requires a mechanical shearing to reduce the liposomal size to less than 0.2 μm for sterile filtration. This is accomplished by sonication or passing the liposomes through a french press device such as a Microfluidizer Model M11-S (Microfluidic International Corp., Newton, Mass.). While considering liposomes prepared from 3β[N-(N',N'-dimethylaminoethane)-carbamoyl]cholesterol in basic form, U.S. Pat. No. 5,283,185, to Epand et al., do not disclose the lyophilization of such liposomes. Lyophilization of liposomes prepared from 3β[N-(N',N'-dimethylaminoethane)-carbamoyl]cholesterol in basic form requires the addition of cryoprotectants such as trehalose to maintain reconstitutability of liposomes.

SUMMARY OF THE INVENTION

Figure 1:
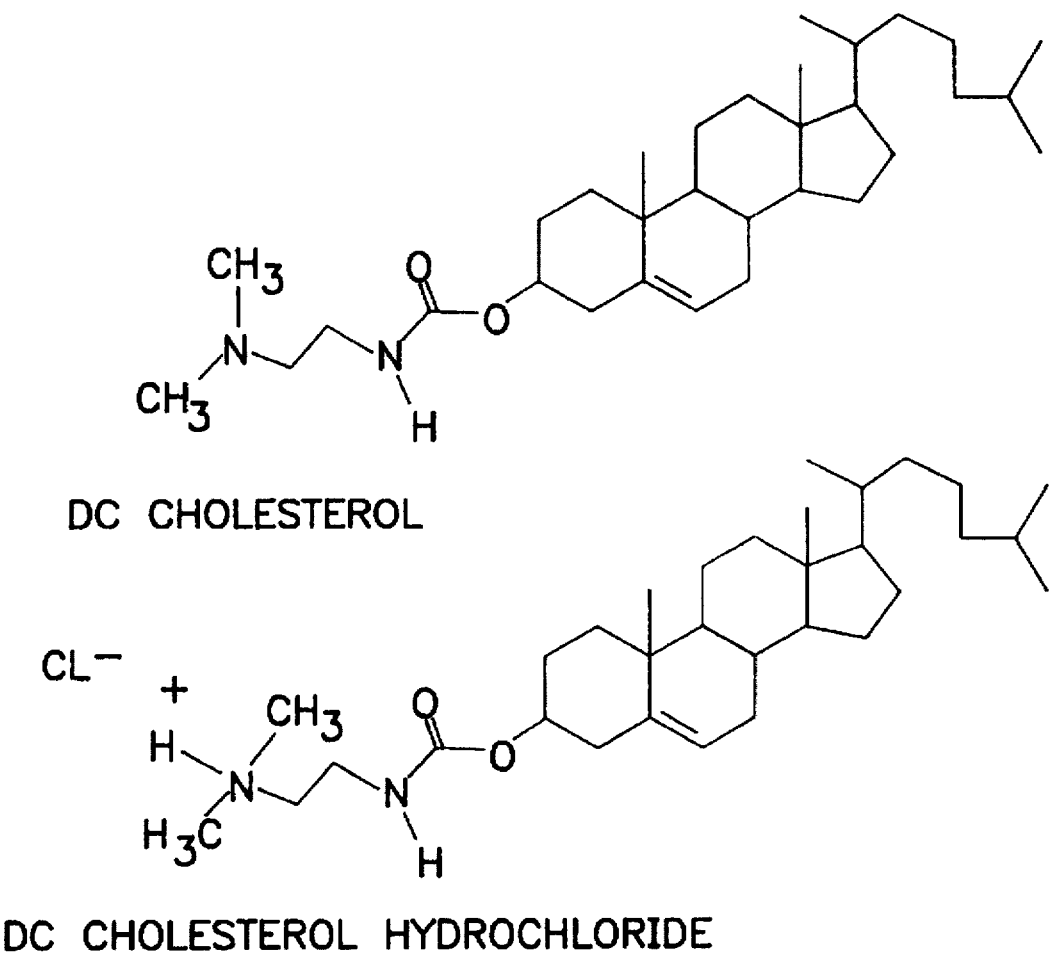
FIG. 1 is a diagram of the chemical structure of basic 3β[N-(N',N'-dimethylaminoethane)-carbamoyl]cholesterol (DC-chol A) as the top structure, and, as the lower structure, 3β[N-(N',N'-dimethylaminoethane)-carbamoyl]cholesterol ("DC-chol B").

This invention comprises the acid salt of the lipid 3β[N-(N',N'-dimethylaminoethane)-carbamoyl]cholesterol ("DC-chol B"), with particular reference to hydrochloride (HCl) salt.

In another embodiment, this invention comprises a transmembrane compatible body hydratable non-liposomal halogenated solvent-free lyophilate comprising 3β[N-(N'N'-dimethylaminoethane)-carbamoyl]cholesterol, with particular reference to the cationic lyophilate and wherein the 3β[N-(N',N'-dimethylaminoethane)-carbamoyl]cholesterol is an acid salt. This invention further includes such lyophilate wherein the 3β[N-(N',N'-dimethylaminoethane)-carbamoyl]cholesterol acid salt is the hydrogenchloride salt. Optionally such lyophilate includes a lipid selected from the group consisting of dioleoyl phosphatidylethanolamine ("DOPE") or dioleoyl phosphatidylcholine (DOPC). In particular embodiments the DOPE constitutes from about 20 mol % to about 80 mol % of the total lipid of the lyophilate, or from about 30 mol % to about 50 mol %. In certain embodiments of the lyophilate the DC-chol constitutes from about 50 mol % to about 70 mol % of the total lipid of the lyophilate. The lyophilate optionally further includes a sugar-class compound, such as dextrose, sucrose, lactose, mannose, and xylose, and particularly mannitol.

In some embodiments this invention comprises a halogenated solvent-free transfecting transmembrane compatible body comprising a 3β[N-(N',N'-dimethylaminoethane)-carbamoyl]cholesterol, and optionally further comprising nucleic acids. In particular embodiments of halogenated solvent-free transfecting transmembrane compatible body, DOPE is further included. It is understood that the 3β[N-(N',N'-dimethylaminoethane)-carbamoyl]cholesterol is basic in some embodiments, and can also be an acid salt (such as the hydrogen chloride salt), or mixtures of the two, and optionally further comprising nucleic acids.

In still further embodiments, this invention comprises a halogenated solvent-free aqueous solution comprising 3β[N-(N',N'-dimethylaminoethane)-carbamoyl]cholesterol wherein substantially all 3β[N-(N',N'-dimethylaminoethane)-carbamoyl]cholesterol is dissolved, and further wherein the solution optionally comprises tertiary butyl alcohol or tBA, particularly wherein the ratio of water to tBA is from about 70:30 to about 0:100, or wherein the percentage of water to tBA is at least about 70%. Reference is also made to such solution wherein the 3β[N-(N',N'-dimethylaminoethane)-carbamoyl]cholesterol is at least about 25% DC-chol B, or at least about 40%, or at least about 60%. Such solution optionally comprises a sugar-class compound, such as dextrose, sucrose, lactose, mannose, and xylose, and particularly mannitol.

This invention includes a halogenated solvent-free aqueous process for preparing a transmembrane compatible body hydratable non-liposomal lyophilate comprising 3β[N-(N',N'-dimethylaminoethane)-carbamoyl]cholesterol comprising the steps of (a) solvating DC-chol in a halogenated solvent-free solvent;

(b) simultaneously or sequentially with step (a) solvating DOPE in said halogenated solvent-free solvent;

(c) lyophilizing said solutions of (a) and (b).

Reference is made to the use of DC-chol contemplates use of DC-chol A and B in a ratio of from about 0:100 to about 100:0, in this process, and particularly wherein said ratio is from about 20:80 to about 40:60. Further, this process contemplates DOPE as present from about 20 mol % to about 80 mol % relative total lipid in the lyophilate, particularly wherein DOPE is present from about 30 mol % to about 50 mol %. This process yet further optionally includes the step of dissolving a sugar-class compound such as dextrose, sucrose, lactose, mannose, and xylose, and particularly mannitol, and most particularly mannitol in the solution prior to lyophilization (simultaneously or sequentially with steps (a) and (b)). Such sugar-class compound is particularly useful in a ratio of from about 0.1% to about 7.5%, and particularly from about 0.5% to about 2%, and further, specific to mannitol, wherein the mannitol is present in the solution prior to lyophilization in a ratio of from about 0.1% to about 7.5%, and specifically from about 0.5% to about 2%.

This invention entails a method of incorporating a sugar-class compound into a transmembrane compatible body hydratable non-liposomal halogenated solvent-free lyophilate comprising 3β[N-(N',N'-dimethylaminoethane)-carbamoyl]cholesterol comprising (a) solvating DC-chol in an aqueous halogenated solvent-free solvent;

(b) simultaneously or sequentially with step (a) solvating DOPE in said halogenated solvent-free solvent;

(c) simultaneously or sequentially with steps (a) and (b) dissolving a sugar-class compound in said halogenated solvent-free solvent;

(d) lyophilizing said solutions of (a)–(c).

In this method the sugar-class compound is usefully selected from the group comprising dextrose, sucrose, lactose, mannose, and xylose, and particularly 20 mannitol. Mannitol is also useful when present in the solution prior to lyophilization in a ratio of from about 0.1 % to about 7.5% or from about 0.5% to about 2%, and the sugar-class compound is particularly useful if present in the solution prior to lyophilization in a ratio of from about 0.1% to about 7.5%, and specifically from about 0.5% to about 2%.

This invention includes a method of introducing bioactive nucleic acid into a cell comprising the step of exposing said cell to a halogenated solvent-free TCB/nucleic acid complex wherein said TCB comprises 3β[N-(N',N'-dimethylaminoethane)-carbamoyl]cholesterol and DOPE, and is absent halogenated solvent.

This invention yet further includes a transmembrane compatible body hydratable non-liposomal halogenated solvent-free lyophilate comprising a lipid which is a cationic lipid acid salt, and optionally further comprising DOPE, and further optionally comprising a sugar-class compound such as dextrose, mannitol, sucrose, lactose, mannose, and xylose. In particular embodiments DOPE constitutes from about 20 mol % to about 80 mol % of the lyophilate as compared with total lipid.

DETAILED DESCRIPTION OF THE INVENTION

Figure 2:
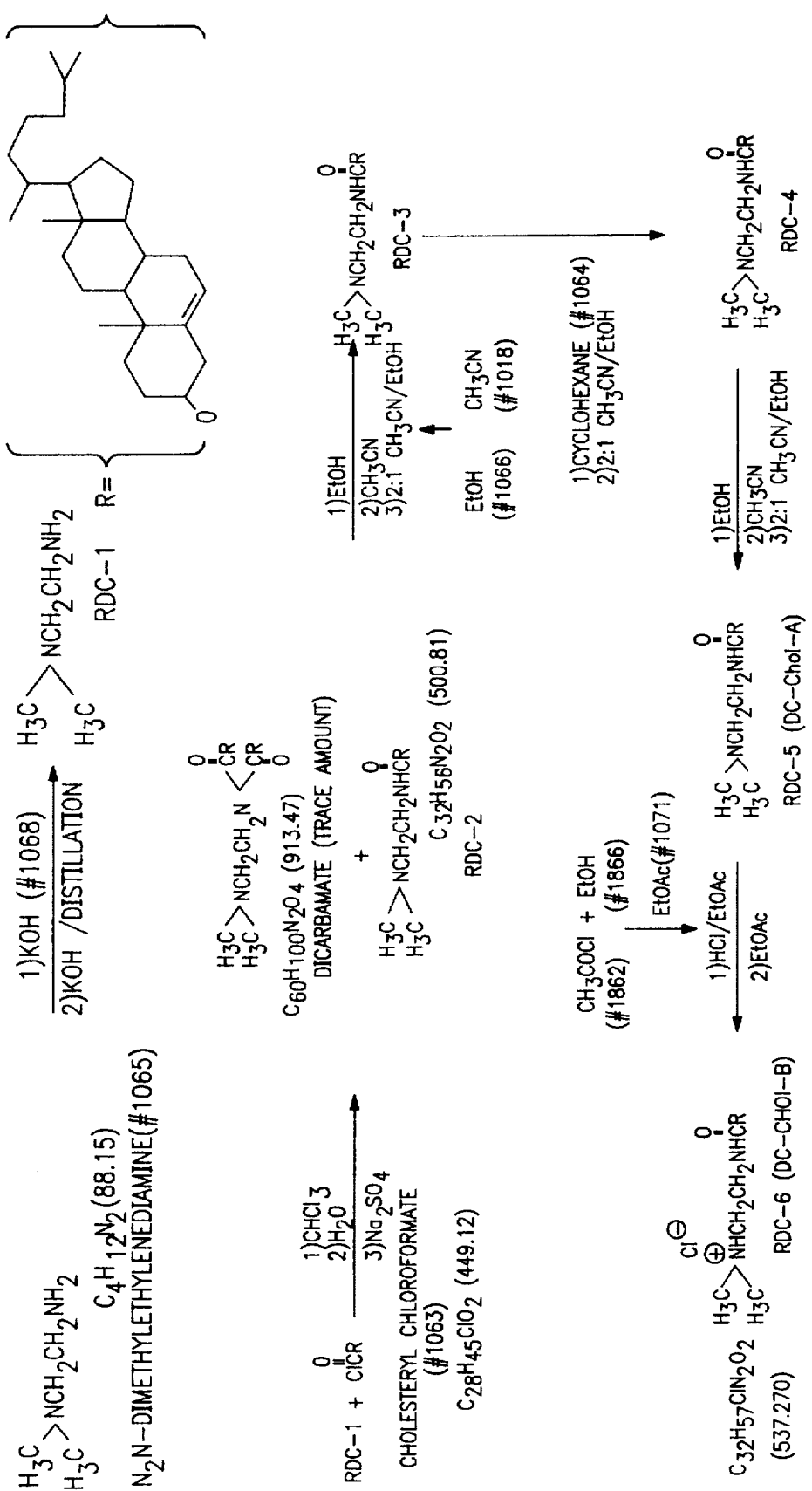
FIG. 2 is a flow diagram of the synthesis of DC-chol B hydrochloride.

For clarity, the following definitions are used herein:

A. 3β[N-(N',N'-dimethylaminoethane)-carbamoyl] cholesterol ("DC-chol B") shall mean a composition in the form of an acid salt as shown in FIG. 1 (there, as the hydrochloride salt, 3β[N-(N',N'-dimethylaminoethane)-carbamoyl]cholesterol hydrochloride) as compared with the basic form. DC-chol B has unique surfactant characteristics as compared to non-acid DC-chol. In addition, DC-chol hydrochloride has a strongly charged amine group. FIG. 2. depicts a flow diagram for synthesis of DC-chol B hydrochloride.

B. Cationic lipids shall include cholesteryl-3β-carboxyamidoethylenetrimethylammonium iodine, 1-dimethylamino-3-trimethylammonio-DL-2-propyl-cholesteryl carboxylate iodide, cholesteryl-3β-carboxyamidoethyleneamine, cholesteryl-3β-oxysuccinamidoethylenetrimethylammonium iodide, 1-dimethylamino-3-trimethylammonio-DL-2-propyl-cholesteryl-3β-oxysuccinate iodide, 2-[(2-trimethylammonio)ethylmethylamino]ethyl-cholesteryl-3β-oxysuccinateiodide, 3β[N-[(N',N'dimethylaminoethane)-carbamoyl]-cholesterol, and 3β[N-[(N',N'dimethylaminoethane)-carbamoyl]-cholesterol, and 3β[N-(polyethyleneimine)-carbamoyl] cholesterol.

C. Acid salts, as applied to cationic lipids shall be used expansively to mean the hydrogen chloride, and quaternary ammonium salts, and more generally the salts of organic and inorganic acids including but not limited to hydrofluoric, hydrobromic, sulfuric, p-toluenesulfonic and phosphoric acids.

Acid salts as applied to of DC-chol B shall be used expansively to mean the hydrogen chloride, and quaternary ammonium salts, and more generally the salts of organic and inorganic acids including but not limited to hydrofluoric, hydrobromic, sulfuric, p-toluenesulfonic and phosphoric acids. The following salts are particularly contemplated: 3β[N-(N',N'-dimethylammonioethane)-carbamoyl]-cholesterol fluoride, 3β[N-(N',N'-dimethylammonioethane)-carbamoyl]-cholesterol bromide; 3β[N-(N',N'-dimethylammonioethane)-carbamoyl]-cholesterol iodide; 3β[N-(N',N'-dimethylammonioethane)-carbamoyl]-cholesterol sulfate; 3β[N-(N',N'-dimethylammonioethane)-carbamoyl]-cholesterol hydrogen sulfate; 3β[N-(N',N'-dimethylammonioethane)-carbamoyl]-cholesterol p-toluenesulfonate; 3β[N-(N',N'-dimethylammonioethane)-carbamoyl]-cholesterol dihydrogenphosphate. Quarternary salts include 3β[N-(N',N'-Trimethylammonioethane)-carbamoyl]-cholesterol salt; 3β[N-(N',N'-Ethyldimethylammonioethane)-carbamoyl]-cholesterol salt; 3β[N-(N',N'-Butyldimethylammonioethane)-carbamoyl]-cholesterol salt; and 3β[N-(N',N'-dimethylpropylammonioethane)-carbamoyl]-cholesterol salt. In this context salts will encompass fluoride, chloride, bromide, iodide, hydrogen sulfate, p-toluenesulfonate, dihydrogen phosphate, and tetrafluoroborate as anion.

D. Transmembrane compatible body ("TCB") shall mean a lipid bilayer body such as a liposome, as well as a micelle, an amorphous amphipathic lipid comprising particle, an aggregate, or an emulsion, any of which traverse a cell membrane under conditions not inconsistent with cell life. By "not inconsistent with cell life" it is understood that the mere conditions of traversal will not cause substantial cell death. This does not exclude the potential for the result of the TCB traversal to be directed to intentionally causing cell death, such as by elaboration of a toxic protein within a cell after such traversal. Nonlimiting examples of such traverse are phagocytosis, endocytosis, apoptosis, intercalation and fusion of the cell membrane with the TCB. In some embodiments, traversal is augmented by techniques such as electroporation or exposure of cell membranes to polyethylene glycol or other membrane solvents.

E. Hydratable shall mean that a powder, upon addition of suitable pharmaceutically acceptable aqueous medium such as water, isotonic saline, 5% dextrose solution, sodium lactate solution, Ringer's solution, Ringer's lactate solution or other aqueous physiologically compatible solutions or combination of solutions, and further including those containing nucleic acids, shall form transmembrane compatible bodies. The term "reconstitutable" is used in the literature when lyophilized liposomes are rehydrated into liposomes. In the present application, the terms "hydrate," "hydratable" and "rehydratable" are preferably employed to stress that the original material was non-liposomal before (as well as after) lyophilization, and until hydration, though in some instances, reconstitutable is used. In particular instances, hydration is accompanied by sonication, stirring or other forms of agitation and mixing.

F. Non-liposomal lyophilate shall mean that the solution lyophilized to form the claimed composition was not in liposomal form at the time of lyophilization. That is, the solution was substantially liposome free before and after lyophilization, and until the point of hydration.

G. Halogenated solvent-free shall mean the absence of halogenated residues, that is less than about 1 ppm. Halogenated residues typically arise from the use of halogenated solvents such as chloroform.

H. Sugar or sugar-class compound shall mean monosaccharides, disaccharides, and further be expansively defined to include sugar alcohols. Sugar-class compounds, include, without limitation, dextrose, mannitol, sucrose, lactose, mannose, and xylose. In the practice of this invention, sugars-class compounds useful as bulking agents for the preliposomal lyophilate. An additional advantage of using sugar-class compounds as bulking agents is that the reconstitution of the TCB may be simplified by reconstitution with sterile water, rehydrating the lipid and sugar thus resulting in a physiologically desirable osmolarity of the TCB suspension. The use of sugar-class compounds as cryoprotectants is not a relevant consideration in the present invention because the solutions from which the preliposomal lyophilates are made are specifically nonliposomal. Thus, there is no gross membrane structure to cryoprotect.

I. Transfecting (or Transfection) shall mean transport of nucleic acids from the environment external to a cell to the internal cellular environment, with particular reference to the cytoplasm and/or cell nucleus. Without being bound by any particular theory, it is understood that transported nucleic acids may be transported as encapsulated, within or adhering to one or more TCBs or entrained therewith. Particular transfecting instances deliver nucleic acid to a cell nucleus.

J. nucleic acids shall be expansively understood to include both DNA and RNA as well as synthetic congeners thereof. Such nucleic acids includes missense, and antisense, nonsense, as well as protein producing nucleotides on and off and rate regulatory nucleotides for control of protein and peptide production and on and off control of nucleic acids production. Particular, but nonlimiting, reference is made to DNA, RNA, and oligonucleotides which are bioactive.

K. Bioactive as applied to nucleic acids indicates a relationship to a biological process.

By way of nonlimiting examples, bioactive includes process which are initiated, accelerated, decelerated, inhibited, enhanced, maintained or otherwise modified, as well as affixation to biological sites resulting in blocking, marking or inactivation of biological processes. Bioactive shall further include diagnostic actions such as marking (i.e., complement DNA probes).

L. Solvating in reference to lipids means dissolving such that there are substantially no liposomes upon said solvation.

M. Dissolving, in reference to sugar-class compounds, means that the sugar-class compound is brought into solution. In an non-aqueous solvent system, such as 100% tBA, additional water must be added to the solvent system to accomplish dissolving, and the addition of such amount of water is entailed in this definition.

Various combinations of DC-chol A, DC-chol B and DOPE are useful in the practice of this invention, with amounts expressed in mole per cent of total lipid. TCB preparations are best comprised of from about 20 to about 80 mol % DOPE, and particularly from about 30 to 50%, and more particularly about 40%. In particular embodiments about 50 to 70 mol % are employed. DC-chol is most useful at from about 20 to about 80 mol %, and particularly from about 50 to 70%, as well as about 30 to 50 mol %, and more particularly about 60%.

Contemplated relative amounts of DC-chol A and B comprise a full spectrum from 100% A to 100% B. For example, halogenated solvent-free 100% DC-chol A preliposomal lyophilate can be prepared in 100% tertiary butyl alcohol (tBA). In particular embodiments, TCBs were prepared with about 40 mol % DOPE and about 60 mol % DC-chol. The DC-chol was employed at five principal molar ratios presented as DOPE:DC-chol A:DC-chol B. These were (a) 4\6\0; (b) 4\4.5\1.5; (c) 4\3\3; (d) 4\1.5\4.5; and (e) 4\0\6.

In the disclosure set forth, relative weights of lipid are generally in mol % of total lipid unless otherwise noted. Amounts of sugar-class compounds are generally expressed as weight per volume unless otherwise stated. Amounts of tBA are generally expressed in volume per /volume unless otherwise stated.

Formulations of TCBs with the foregoing ratios of DC-Chol A or B and DOPE 20 were dissolved in a solvent mixture ranging from 100% tertiary-butyl alcohol to 30% tBA:70% water. Note that tBA is a non-halogenated solvent whose freezing point and vapor pressure are well suited for use in the practice of lyophilization. The formulated solutions of lipid and solvent were clear and essentially particle free. Such formulations in which the components form a clear solution lead to several advantages. Specifically, the solution can be sterile filtered and subsequently aseptically filled to give a sterile lyophilized vial of pre-liposomal TCB. This is a distinct advantage over the method disclosed by U.S. Pat. No. 5,283,185 (Epand et al.) -which requires size reduction of the DC-Chol liposomes by mechanical stress prior to filtration. Additionally, in preparations of the instant invention in which the lipids are not in the form of liposomes prior to lyophilization, and which result in a non-liposomal lyophilate, allow the preparation of the lyophilized TCB without cryoprotectants, since no liposomal particles are present to cryoprotect during lyophilization.

In the practice of this invention, using sugars and sugar alcohols as bulking agents was advantageous. Specifically, the use of a low concentration of mannitol (about 1 % to about 2% by weight) in the formulation provided a means of generating TCBs of smaller size compared to lyophilization without mannitol. The use of mannitol in this manner had several advantages: by adding bulk, it enhanced the rehydration of the TCB; and contributed to the osmolarity of the reconstituted TCB; in addition to reducing the rehydrated TCB particle size. In the practice of this invention, smaller cationic liposomes are preferred, however, our experience shows that TCBs in the range of about 300–1000 nm are equivalent with respect to in vitro transfection. Another embodiment utilized sucrose at a concentration in the TCB preparation such that, when reconstituted to the desired volume with water, the TCB was iso-osmotic, and the final sucrose concentration was 300 mM. TCBs prepared in this manner rehydrated to relatively smaller sizes. Use of 30 mM and 50 mM sucrose in this manner allows for simplified reconstitution.

A primary application of TCB lies in the ability to deliver nucleic acids to cells. The mixing of the nucleic acids with the rehydrated TCB has been throughly investigated. One method is described below. Several factors affect the size stability of the TCB/nucleic acids complex including: their relative concentrations, the volume in which they were mixed, and the composition of the injectable solution. An example of a preferred embodiment is the following:

Preparation of a TCB/nucleic acids complex to give a final concentration of 25 ug/mL DNA: 250 nmoles/mL (155 ug/mL) lipid where the DNA solution and the TCB solution were mixed in equal volume.

TCB dosage form was composed of a 30 cc flint glass vial (a first vial) containing a total mg lipid equivalent 6.2 mg/vial with DC-chol B and DOPE in a 6:4 mole ratio, is where the TCB was lyophilized with 1% mannitol, and then rehydrated with 20.0 mLs of 5.0% dextrose in water. This resulted in a final concentration of lipid in the vial equivalent to 500 nmoles/mL (310 ug/mL).

The nucleic acids was presented in a 30 mL glass vial (the second vial) filled with 1 mg of DNA in 1 mL of Tris 3 mM, 0.3 mM EDTA in sterile water, resulting in a concentration of nucleic acids equivalent to 1000 ug/mL. To this second vial 19 mL of 5% dextrose in water was added to yield a concentration of the DNA equivalent to 50 ug/mL.

Equal volumes of the nucleic acids vial contents and the TCB vial contents were gently mixed in a vial (the third vial) to give a final concentration of 25 ug/mL DNA: 250 nmoles/mL (155 ug/mL) lipid.

The compositions of this invention possess valuable pharmacological properties. TCBs facilitate administration of nucleic acids as therapeutic agents or diagnostic agents. In some embodiments, nucleic acids so administered produces proteins after entry into the subject cells. Such proteins, in particular protocols are markers. Such compositions can display antineoplastic effects, antiviral effects, immunomodulation, hormone mediated effects or modulation of and compensation for metabolic anomalies or defects. In human and veterinary medicine, these effects can be demonstrated, for example, using the method of directly introducing TCB's in association with nucleic acids into a subject. Useful routes of administration include intraperitoneal delivery, intrapleural, subdural, intrathecal, intramuscular, intratumor, subcutaneous, buccal, sublingual, intravenous ("i.v.") (which may be is general or in a delivery loop to a more specific site), intraarterial, or parenteral delivery, and further including aerosols (e.g., nasal spray). In some embodiments i.v. delivery augments delivery to the reticuloendothelial system. In another embodiment, treatment is of cells by in vitro or extracorporeal methodology. In some applications based on in vitro or extracorporeal methodology, cells are treated outside of an animal and then reintroduced into the animal.

In particular protocols, such as certain protocols those treating highly proliferative cells, modulation of metabolic defects, or when provoking an immune response, treatment will not be (in most instances) dose dependent, beyond mere threshold considerations. Some uses (such as diagnostic uses with radiolabeled nucleotides), however, are more usually dose dependent.

The size of the TCB's is noteworthy. A characteristic of TCB's hydrated from preliposomal lyophilates with at least about 25% DC-chol B provides TCBs with a mean diameter of 550±225 nm when reconstituted, when the TCB lyophilate was prepared from 50:50 tBA:water mixture.

These compositions can be used to deliver intracellular therapeutics to treat a variety of conditions including without limitation (i) metabolic and genetic diseases, (ii) infectious diseases including bacterial and viral conditions, (iii) parasitic diseases, (iv) neoplastic diseases, as well as (v) delivery of vaccines against infectious diseases, tumors, and parasites. Yet further, these compositions contemplate treatment of AIDS, and those medical conditions which responding to variation in protein production. However, the composition and method of this invention is particularly useful for the amelioration of neoplastic conditions including cancer and psoriasis. It is further useful for treating conditions associates with inappropriate, abnormal cell proliferation, (whether over or under producing) and non-native cell proliferation.

The compositions of this invention are generally administered to animals, including but not limited to livestock (such as cattle and poultry), household pets such as cats, and dogs, and also to humans, etc.

The pharmacologically active compositions of this invention can be processed in accordance with conventional methods of Galenic pharmacy to produce medicinal agents for administration to subjects, e.g., mammals including humans.

The compositions of this invention can be employed in admixture with conventional excipients, i.e., pharmaceutically acceptable organic or inorganic carrier substances suitable for oral, parenteral, inhalation or topical application which do not deleteriously react with the active compositions. Suitable pharmaceutically acceptable carriers include but are not limited to water, salt solutions, buffer solutions, protein solutions (such as albumen), carbohydrates such as sugars or sugar alcohols including dextrose, sucrose and mannitol. The pharmaceutical preparations can be sterilized and/or mixed with substances and the like which do not deleteriously react with the active compositions. Vials or ampules are convenient unit dosages, such as one containing the preliposomal lyophilate, and, optionally, nucleic acids, such as a plasmid. In one embodiment, the preliposomal lyophilate is in a sterile vial to which is added plasmid nucleic acids, water and sugar or sugar alcohol. A particular mixture comprises water for hydration which is 5% dextrose.

Sustained or directed release compositions are particularly contemplated. The wide variety of effects for which the nucleic acids is introduced yields an equivalently large number of useful dosages. The practitioner skilled in the art will appreciate that administration is usefully "titrated" up to an efficacious dose. Thus, it is convenient to administer small doses until a particular response is detected, to arrive at a final dosage.

It will be appreciated that the actual preferred amounts of active compositions in a specific case will vary by subject as well as by the specific compositions being utilized, the particular compositions formulated, the mode of application, and the particular sites and organism being treated. Dosages for a given host can be determined using conventional considerations, e.g., by customary comparison of the differential activities of the subject compositions and of a known agent, e.g., by means of an appropriate, conventional pharmacological protocol. The present invention is further illustrated by the following non-limiting examples.

EXAMPLE 1

TCB Preparation

DC-chol A:DC-chol B:DOPE was prepared into TCBs of the following constituents (presented as molar ratios): (a) 6\0\4; (b) 4.5\1.5\4; (c) 3\3\4; (d) 1.5\4.5\4; and (e) 0\6\4. All formulations were prepared at above 30° C. and at atmospheric pressure. Mixing was via stir bar at approximately 500 rpm. All solutions were stirred until clear and then aliquotted. Forty aliquots of equal weight (total ingredients) of each solution were placed (one each) into 30 cc flint vials with a 20mm opening. Each vial contained about 10 mL prior to lyophilization.

TABLE 1

| A:B:DOPE (molar) | DCchol A (g) | DCchol B (g) | DOPE (g) | tBA (g) |
| --- | --- | --- | --- | --- |
| (a) 6\0\4 | 0.240 | 0.0 | 0.238 | 7.65 |
| (b) 4.5\1.5\4 | 0.180 | 0.064 | 0.238 | 7.65 |
| (c) 3\3\4 | 0.120 | 0.129 | 0.238 | 7.65 |
| (d) 1.5\4.5\4 | 0.060 | 0.193 | 0.238 | 7.65 |
| (e) 0\6\4 | 0.0 | 0.258 | 0.238 | 7.65 |

Each of the solutions (a) through (e) was lyophilized (FTS Dura-Top MP model TDS-2C-MP [Stone Ridge, N.Y.]), and then hydrated (injected with ambient temperature diluent into an ambient temperature lyophilization vial of formulation with 10 mL ultrapure water. A cloudy suspension of TCBs resulted, which was tested for size by photon correlation spectroscopy or PCS. Following mixing with nucleic acids, the resulting TCB/nucleic acids complex was tested by via transfection bioassay, particle sizing and direct observation.

Transfection Assay: The luciferase transfection assay provides a means of determining the capability of TCB preparations to deliver plasmid DNA. In this case, the plasmid DNA encodes the firefly luciferase reporter gene and can be detected in a rapid and sensitive assay where the luciferase protein reacts with its substrate, luciferin, causing a release of light. The light intensity is a measure of the luciferase protein and therefore a measure of the delivery of plasmid DNA to cells.

Hydration of TCB and addition of nucleic acids: Plasmid DNA dissolved in 3 mM Tris, 0.3 mM EDTA buffer pH 8.0 was either added directly to TCBs or was diluted first in an appropriate dilution medium (such as 5% dextrose or other injectable fluids) and then added to the resuspended TCBs. Following gentle mixing the TCB/plasmid DNA complex held at room temperature for 10 min to 4 hours.

The TCB/plasmid DNA complex was then diluted with tissue culture medium and then added to tissue culture cells, such as CHO (Chinese hamster ovary) cells. This TCB/plasmid DNA complex was allowed to incubate with the cells for 4 hours at 37° C. The medium containing the TCB/plasmid DNA complex was removed from the cells and then the cells were incubated for an additional 2 days at 37° C. to allow for expression of the luciferase protein by the cells that have taken up the plasmid DNA. When transfection was successful a crude protein extract from the cells reacted with luciferin substrate producing light which was detected with a luminometer (Berthod Lumat, model LB9501, Wallac, Inc, Gaithersburg, Md.)

Luminescence was measured as raw light units (RLU) and a calibration curve for protein allowed calculation of specific activity as luminescence /protein RLU/mg protein.

Particle sizing: Particle sizing as a determination of particle diameter was performed using photon correlation spectroscopy (PCS) according to manufacturers specifications (Brookhaven Instruments PCS, model B1-9000AT, Brookhaven, N.Y.) interfaced to a Compaq PC. An Argon 633 nm cylindrical laser was used as the light source. All measurements were performed at 90°, the angle of lowest contaminant scattering.

Sample work-up for TCB involved resuspension to 2000 nmol/mL in various solvents, with particular reference to: 300 mM dextrose, 300 mM sucrose, 300 mM mannitol, 150 mM saline, 5% dextrose injection, and sterile water. Approximately 600 to 1000 µL was placed into 4 mL test glass culture tubes. Tubes were subsequently wiped down with methanol using a low lint Kim-wipe™, checked for scratches, and inserted into a decalin bath.

All samples were measured using a special test-tube adapter. Samples resided in a glass vat bathed in decalin at about 25° C. Samples were adjusted for counts and baseline using a test run by adjusting the first and last delays (time sample detection). Proper sample collection times yielded a sigmoidal curve with a less than 1% baseline difference. After adjustments, samples were measured for 60 seconds. Afterwards, a cumulant analysis was performed for which quadratic size and polydispersity data as well as Kcounts and percent baseline (measured vs. calculated) were recorded. Cumulant data was printed out and tabulated. An example summary of average for TCBs reconstituted in water and diluted as shown is given in Table 2.

TABLE 2

| Diluent | Diam, nm | Polydisp. | Kcnts/sec. | Base % diff. |
|---|---|---|---|---|
| Control-water | 674.0 | 0.277 | 200.013 | 0.196 |
| Sucrose(300 mM) | 471.1 | 0.277 | 290.248 | −0.223 |
| Saline(150 mM) | 532.2 | 0.295 | 313.477 | −0.498 |
| Dextrose(5%) | 464.5 | 0.242 | 280.840 | 0.039 |

(TCB was reconstituted in water and subsequently diluted with the listed diluent.)

Appearance of the vial and lyophilate cake were considered as a determinant of product quality and a predictor of hydratability. All five cakes of the present example were off-white in color. Some material adhered to the sides of the vials.

Hydration of the lypohilate was performed at room temperature (25° C.) with water.

Table 3 sets forth the results of the inspection of the product of (a) through (e).

TABLE 3

| A:B:DOPE (mole ratio) | transfection RLUx $10^3$/mg | TCB mean dia. nm | lyophilate cake observation | hydration at 25° C. |
|---|---|---|---|---|
| (a) 6\0\4 | ~1885 | ~700 | thin (~1 cm), cratered on top, top and sides concave, fibrous. tightly interwoven strands, white with residue on vial walls | suspension with particles which settle |
| (b) 4.5\1.5\4 | ~3375 | ~659 | ~1 cm cake, concave center ~0.5 cm; fibrous; interwoven strands, white with residue on vial walls | immediate suspension hand mixing |
| (c) 3\3\4 | ~2206 | ~414 | mound shape with concave center, ~1 cm cake, slightly concave sides; loosely interwoven strands, white with residue on vial walls | immediate suspension, hand mixing |
| (d) 1.5\4.5\4 | ~1788 | ~311 | annular or toroidal cake; ~0.75 cm thick; concave center; interwoven strands, white with residue on vial walls | immediate suspension, hand mixing |
| (e) 0\6\4 | ~1032 | ~273 | slight concave depression; highly fibrous with some tight and some loose interwoven strands, white with residue on vial walls | immediate suspension, hand mixing |

EXAMPLE 2

DC chol A in 100% tBA

As described in Example 1, TCBs of DC-chol A and DOPE (without DC-chol B) were made in 100% tBA. This particular embodiment has been prepared in 30-cc. flint glass vials with an inner diameter of ~3.25 cm, in 30-cc vials with an inner diameter of ~2.50 cm and in 5-cc vials. The TCB lyophilates prepared with 100% DC-chol A showed some relationship to cake thickness with a thinner cake giving a preferred rehydrated TCB. The preparations made in the 30-cc, 3.25-cm ID vials and the 5-cc vials always a preferred TCB solution when hydrated. Those prepared in 2.50-cm ID vial, in some instances, generate particulates. Brief sonication of the solution, however, often reduces the degree of particulation. A typical example of embodiments made in 30-cc vials of ID ~3.25 cm is a TCB size of 723±37 nm and a transfection result of 468 RLUx$10^3$/μg when mixed with plasmid DNA. Samples (b) through (e) did not exhibit particulation upon hydration, regardless of vial type.

EXAMPLE 3

DC-chol B in 100% to 30% tBA

Figure 3:
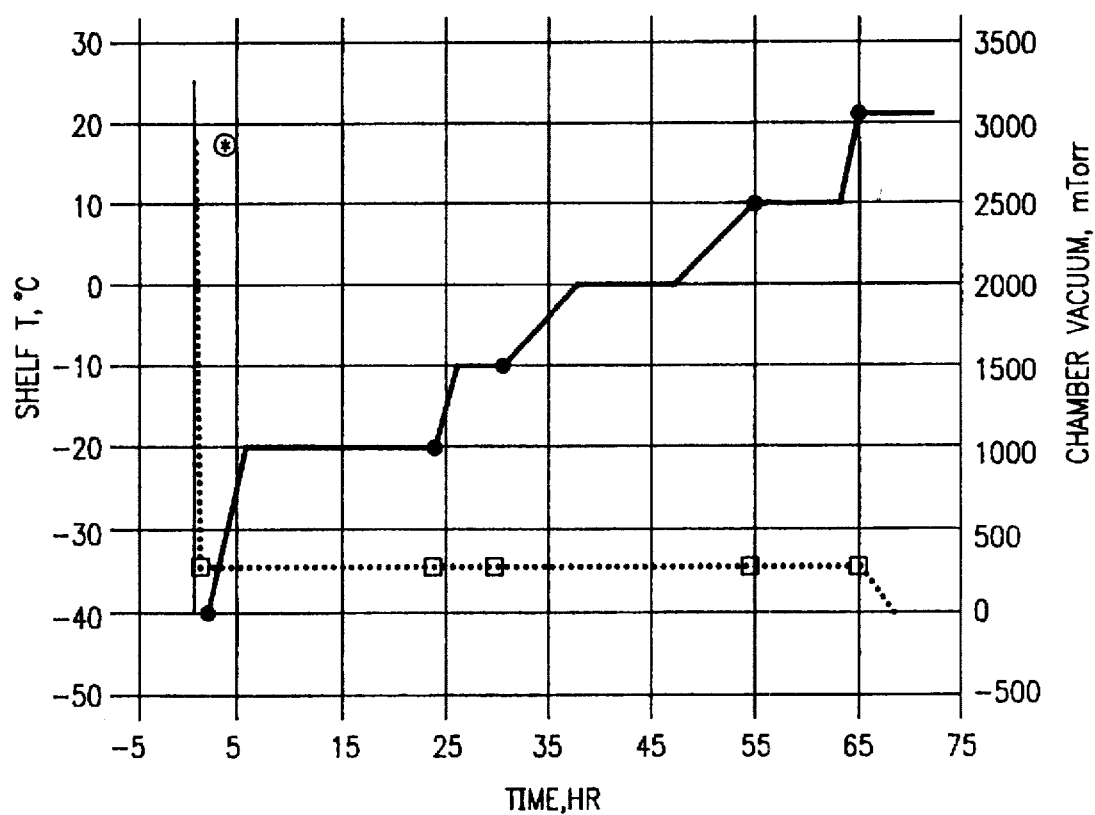
FIG. 3 is a time, temperature, pressure graph of particular lyophilization cycle.

Four different tBA/H$_2$O systems were used to prepare vesicles: 10/0, 8/2, 5/5 and 3/7 (v/v). Formulations were made using 12 μmol of DC-chol B and 8 mmol of DOPE dissolved in 10 mL of each of the four solvents mixtures. Lyophilates were then prepared as in Example 1, but using a cycle designed to take the preliposomal solutions from 25° C. down to −40° C. and ramped over various time periods back to 25° C. One such cycle is presented in FIG. 3. In FIG. 3, the solid line represents temperature and the dotted ;line represents pressure. Lyophilization was at atmospheric pressure (760000 mTorr) during freezing [graphed at 3000 m Torr for scale convenience), 300 m Torr for primary drying, and then approximately 15 mTorr or mm Hg of pressure was applied during the later stages (secondary drying—from about 0° C. to about 25° C.) to achieve complete drying. Complete lyophilization was accomplished over about 3 to 4 days. All four solvent systems yielded a lyophilized product similar to those of Example 1, (b) through (e).

In applications using 100% tBA, caution must be employed because its freezing point is 23° C. Thus care in aliquotting into the lyophilization vials is indicated. A particular embodiment with favorable characteristics of appearance and ease of hydration of the lyophilized cake in conjunction with UV turbidity data was a solvent system of a 50/50 (v/v) mix of tBA/H$_2$O (see Example 7). Favorable appearance was that of a compact off-white cake formed with interwoven strands and a concave depression on the top. The cake and any material on the sides of the vial are readily rehydrated in the chosen aqueous solution with hand agitation or brief sonication to a cloudy suspension of TCBs without visible aggregation.

EXAMPLE 4

Preparation of transmembrane compatible body hydratable non-liposomal halogenated solvent-free lyophilate comprising 3β[N-(N',N'-dimethylaminoethane)-carbamoyl]cholesterol TCB was a 0\6\4 DC-chol A\DC chol B\DOPE lipid mixture. To produce a forty-vial batch of TCB, 1.2 μmol of DC-chol B and 0.8 μmol of DOPE powders were dispensed by mass into a flint glass vials. Into each vial was aliquotted 38.3 g of tBA. The resulting mixture was stirred at approx. 500 rpm on a heated (to ~30° C.) plate until total dissolution of the lipids. After the solution became clear, 49.4 g of ultrapure water was added to the reaction bottle with mixing. Again the mixture was stirred to clarity to ensure homogeneity. This took about 20–30 min for volumes ≧ 500 mL. After thorough stirring, the mixture was aliquotted by mass individually into the forty labeled vials, the vials were loosely stoppered, placed in the lyophilizer and then lyophilized to dryness, using the lyophilization program described in Example 3. The vials were then stoppered tightly under vacuum, removed from the lyophilizer and sealed.

EXAMPLE 5

Use of Sugar-class compounds in TCB

Sugars have played a two-fold part in the developing formulation: that of a potential bulking agent (pre-lyophilization) and that of a diluent (post-lyophilization).

EXAMPLE 5A

Use of Sugar and Sugar Alcohols as Bulking Agents

Absent bulking agents, the lyophilates of this invention (lipidic cakes which result after lyophilization) were generally compact and flat. A flat cake, while useful, was less convenient for monitoring the temperature of the cake. Difficulty arose in maintaining intimate contact of the lyophilate with a thermocouple during lyophilization. Sugar-class compounds do not dissolve in 100% tBA and therefore do not integrate well into a totally non-aqueous formulation. Sugar crystals tend to remain as crystals throughout lyophilization. When using sugar-class compounds it was preferable to first dissolve the compound in water before combining it with the remainder of the formulation ingredients.

Sucrose, mannitol, dextrose and xylose were integrated into the formulation and is then lyophilized, with varying cake results. When hydrated with ultrapure water, samples of 0\6\4 TCBs ranged in size (by PCS) on average from 223 nm to 542 nm. Table 4 below. Turbidity measurements (by the method of Example 7) showed that mannitol at a concentration of 300 mM, upon hydration, yielded less stable TCBs over time compared with dextrose or non-sugar-class compound TCBs. mannitol in lesser concentrations, 1% (55 mM)]better maintained TCB size stability.

TABLE 4

| Sugar in lyophilate {concentration = 300 mM} | PCS diameter, nm | Transfection Bioassay RLU × 10³/μg |
|---|---|---|
| none (control) | 516 | 276 |
| mannitol | 542 | 479, 880* |
| sucrose | 223 | 457 |
| xylose | 320 | 472 |
| dextrose | 353 | 358 |

*mean of two measurements

Studies of the post-lyophilization use of sugar-class compounds as diluent (hydrating) solutions were performed in tandem with the use of pre-lyophilization sugar-class compounds in formulation. In terms of mannitol-laden TCB, when made with mannitol to a final concentration 1% (55 mM), the resultant TCBs, when hydrated, behave well. The cakes hydrate with ease, the cakes were fluffy and full, with pharmacologically suitable TCB size stability. These formulations exhibited enhanced size stabilization when the TCB was mixed with the plasmid DNA. Mannitol-free TCBs (no sugar-class compounds) averaged 515 nm in diameter when formed and 884 nm when complexed with nucleic acids. TCBs with 1% mannitol averaged 407 nm in diameter when formed and 913 nm when complexed with nucleic acids.

Among TCB complexed plasmid sizes studied (via PCS), preferred TCB formulations included: 1% mannitol, 2% mannitol, and no sugar (control). Mannitol was selected as a preferred sugar for its properties as a bulking agent and ease of reconstitution and smaller relative liposomal average size (400 nm to 600 nm). As a complex, the control (no sugar in lyophilate) measured approximately 800 to 1100 nm on average. While the no sugar product was useful, the bulk contributed by the presence of sugars made manipulation of the lyophilate easier. No noticeable size differences have been observed in either 1% and 2% mannitol. Sizes consistently average between 500 and 900 nm. Both freshly reconstituted TCB's and TCB complexed with nucleic acids (here, luciferase or EIA plasmid) were sized.

5B: Sugar-class compounds as a Diluent

In order to determine the effect which sugar or salt containing solutions had on TCBs when used to hydrate, ten solutions were tested as alternative diluents: 5% dextrose in water, 2.5% dextrose in ½-strength lactated Ringer's solution, sodium lactate in water, a 50/50 volume mix of 5% dextrose and sodium lactate, lactated Ringer's solution, 5% dextrose solution with 0.2% NaCl, 5% dextrose solution with 0.45% NaCl, 5% dextrose in lactated Ringer's injection solution, 0.9% saline, and 300 mOsm dextrose in water and 300 mOsm sucrose in water. These tests showed a range of compatibility with the TCB to perform as desired. Results from testing with the UV turbidity screening assay(as discussed in Example 7), and the transfection assay (Table 5) suggest a advantages of the use of 5% dextrose in water for reconstitution of the lyophilized TCB and prior to mixing with DNA, because this results in a relatively stable size of the complex of the over time following nucleic acids complexation.

TABLE 5

| Sugar Diluent Solution | Transfection Assay Results, RLU × 10³ |
|---|---|
| 5% dextrose in water | 301 ± 70 |
| 2.5% dextrose in A-strength lactated Ringer's solution | 377 ± 183 |
| sodium lactate in water | 396 ± 313 |
| 50\50 volume mix of 5% dextrose and sodium lactate | 46 ± 5 |
| lactated Ringer's solution | 70 ± 25 |
| 5% dextrose solution with 0.2% NaCl | 71* |
| 5% dextrose solution with 0.45% NaCl | 245* |
| 5% dextrose in lactated Ringer's injection solution | 304 ± 301 |
| 0.9% saline | 232 ± 110 |
| 300 mOsm dextrose in water | 342 ± 88 |

*only one replicate measurement was made

EXAMPLE 6

Complex Stability

An important aspect of this invention is the preparation of a stable TCB/nucleic acids complex; that is stable complexes relative to complex size. DC-chol A Liposome/ nucleic acids prepared as described in U.S. Pat. No. 5,283, 185 (Epand) increase in size as a function of time. Such instability can affect the pharmaceutical utility and reproducibility of response. The effect of several variables on the size stability of the TCB/nucleic acids complex are listed below.

TABLE 6

|  | Effect on Stability |
|---|---|
| Decreasing the total lipid & DNA concentration | Increased |
| Decreasing the DNA:Lipid total mass ratio | Increased |
| Use of 3 mM Tris pH 8, 0.3 mM EDTA | Increased |
| Use of Mannitol as a bulking agent for TCB | Increased |
| Reconstitution of TCB with 5% Dextrose in water or with sterile water for injection | Increased |
| Reconstitution of TCB with Salts or Media | Decreased |

Several methods have been used to determine the trends including, mixing with visual monitoring of aggregation upon mixing, turbidity, transfection and sizing by PCS.

EXAMPLE 7

Monitoring size stability of the TCB/nucleic acids complex.

Turbidity was determined via Varian Cary 3e UV-VIS Spectrophotometer. Within its DOS-based kinetic program, measuring changes in absorbance over time. A stable liposomal solution is at a constant initial absorbance. As nucleic acids is added, liposomes form complexes with plasmid nucleic acids. TCB's complexed with nucleic acids alter the turbidity, or cloudiness of the solution increasing the particle size. Hence, a change in light scattering, or absorption result. The tracing of time vs absorbance demonstrates changes in the stability of the complex over several time points beginning at time zero (before nucleic acids addition). The goal is to achieve a TCB/nucleic acids complex which is size stable over time.

To test stability, TCBs are prepared as described in Example 3. Thereafter, samples were measured approximately every 1 to 5 minutes at 600 nm., for a period of two to four hours. Samples contain 500 nmol/mL TCB and 50 mg/mL plasmid DNA. Hydration and proper dilutions are made with 5% dextrose. Final concentrations and volumes have not been completely resolved. For lab-scale usage, samples are prepared in approximately 1 mL aliquots. The lipid component was (here DOPE and DC-chol) prepared in 2 mL flint injection vials. Plasmid is prepared in 1 mL micro-centrifuge tubes. Afterwards, plasmid is combined with TCB in the flint vials and inserted into pre-set sample cuvettes in a special application 12 cell multi-cell holder. A reference (blank) cuvette with 5% dextrose is included in cell twelve. Thereafter, the program is immediately started. During sample work-up (DNA injection) time is kept, and consequently, added to the assay cycle time during data work-up.

Figure 4:
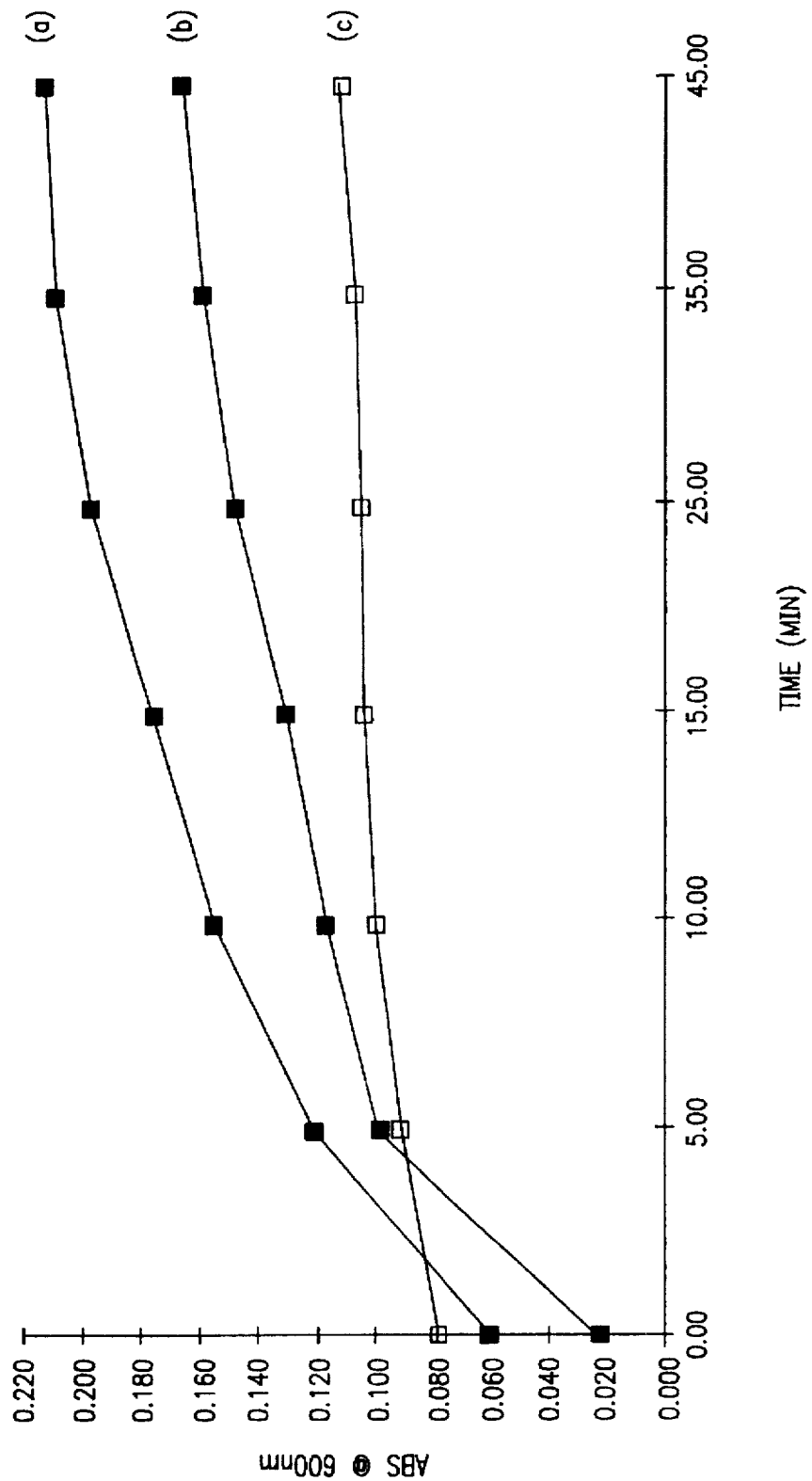
FIG. 4 is a size and stability over time data presentation of transmembrane compatible body ("TCB")/DNA complexes after mixing.

An example of the utility of the assay follows. Samples were measured every 30 seconds for 45 to 60 minutes. Sample work-up included 30 µL TCB (2000 nmol/mL), 6 µL plasmid (1 µg/µL), and 564 µL diluent (identical to reconstitution is solvent), a plasmid DNA: TCB ratio of 1:20. TCB's were reconstituted in various diluents including 300 mM dextrose, 300 mM mannitol, 300 mM sucrose, 150 mM saline, 150 mM sodium lactate, 5% dextrose, and a 50/50 mixture of 5% dextrose and sodium lactate. Size stability data over time is presented as FIG. 4, wherein 150 mM sodium lactate is represented as line (a), 5% dextrose as line (c), and the 20 50/50 mixture of 5% dextrose and sodium lactate as line (b). Selection of reconstitution solvent was based on (a) minimal increase in absorbance within the first 10 minutes (complexation), and (b) minimal change absorbance over the remaining assay as parameters indicative of size stability. An example diluent screening assay is given below.

EXAMPLE 8

Preparation of DC-chol B

To a solution of N,N-dimethylethylenediamine (30.5 mL, 24.7 g, 278.4 mmol), distilled from potassium hydroxide under nitrogen in chloroform (61 mL) solution of cholesteryl chloroformate (20.8434 g, 46.45 mmol) in chloroform (121 mL) was dropwise added at −10° C. with energetic stirring. Reaction mixture was stirred for an additional 10 minutes and water (30.5mL) was dropwise added. The mixture was then transferred to a separatory funnel and washed three times with water (3×100 ml) and dried over sodium sulfate. Thin layer chromatography (CHCl$_3$/MeOH 65:35, fr 0.6) revealed complete conversion of substrate. After filtering off sodium sulfate, solvents were evaporated in vacuo and crystallizing oil was dried in vacuo (16h, 0.1 mbar, 20°–25° C.), yielding 23.3 g of material. This material was then crystallized from an ethanol/acetonitrile mixture, cyclohexane, and again from ethanol/acetonitrile to yield 18.6171 grams of fine, colorless crystals of 3β[N-(N',N'-dimethylaminoethane)-carbamoyl]cholesterol.

To a stirred solution of 4.8563 g of 3β[N-(N',N'-dimethylaminoethane)-carbamoyl]cholesterol in ethyl acetate (50 mL) 1M solution of hydrogen chloride in ethyl acetate (9.7 mL, 9.7 mM) was dropwise added at 20°–25° C. Reaction mixture was stirred for an additional 10 minutes and was diluted with ethyl acetate (30 mL). Precipitate was then filtered through a Buchner funnel and washed with several portions of ethyl acetate (6×25 mL) until neutral pH. Precipitate was dried in vacuo (16h, 0.1 mbar, 20°–25° C. to yield 4.8463 g 3β[N-(N',N'-dimethylaminoethane)-carbamoyl]cholesterol hydrochloride. This scheme is also set forth in FIG. 2.

What is claimed:

1. The acid salt of 3β[N-(N',N'-dimethylaminoethane)-carbamoyl]cholesterol ("DC-chol B").

2. The compound of claim 1 wherein said acid salt is the hydrochloride (HCl) salt.

3. A transmembrane compatible body prepared from a hydratable non-liposomal halogenated-solvent-free lyophilate comprising the lipid 3β[N-(N',N'-dimethylaminoethane)-carbamoyl]cholesterol ("DC-chol") wherein the lyophilate is cationic.

4. The lyophilate of claim 3 wherein the 3β[N-(N',N'-dimethylaminoethane)-carbamoyl]cholesterol is an acid salt.

5. The lyophilate of claim 4 wherein the 3β[N-(N',N'-dimethylaminoethane)-carbamoyl]cholesterol acid salt is the hydrogenchloride salt.

6. A halogenated solvent-free transfecting transmembrane compatible body comprising an acid salt of a 3β[N-(N',N'-dimethylaminoethane)-carbamoyl]cholesterol further comprising nucleic acids.

7. The transfecting transmembrane compatible body of claim 6 wherein the acid salt is the hydrogen chloride salt.

8. A halogenated solvent-free solution comprising at least about 25 mol % DC-chol B.

9. The solution of claim 8 comprising at least about 40 mol % DC-chol B.

10. The solution of claim 9 comprising at least about 40 mol % DC-chol B.

11. A halogenated solvent-free process for preparing a transmembrane compatible body from a hydratable non-liposomal lyophilate comprising the lipid 3β[N-(N',N'-dimethylaminoethane)-carbamoyl]cholesterol (DC-chol) comprising the steps of (a) solvating DC-chol in a halogenated solvent-free solvent;

(b) simultaneously or sequentially with step (a) solvating the lipid DOPE in said halogenated solvent-free solvent;

(c) lyophilizing said solutions of (a) and (b).

wherein said DC-chol is DC-chol A and B in a concentration of from about 0:100 to about 100:0.

12. The process of claim 11 wherein said concentration is from about 20:80 to about 40:60.

13. A halogenated solvent-free transfecting transmembrane compatible body comprising a cationic 3β[N-(N-(N', N'-dimethylaminoethane)-carbamoyl]cholesterol.

* * * * *

UNITED STATES PATENT AND TRADEMARK OFFICE
CERTIFICATE OF CORRECTION

PATENT NO. : 5,753,262
DATED : May 19, 1998
INVENTOR(S) : Wyse et al.

It is certified that error appears in the above-indentified patent and that said Letters Patent is hereby corrected as shown below:

Column 17, lines 3 and 4 (corresponding to claim 10) should read -- The solution of claim 9 comprising at least about 60 mol % DC-chol B. --

Signed and Sealed this

Fourth Day of August, 1998

Attest:

BRUCE LEHMAN

Attesting Officer     Commissioner of Patents and Trademarks